(12) United States Patent
Wang

(10) Patent No.: US 11,387,416 B2
(45) Date of Patent: Jul. 12, 2022

(54) ORGANIC LIGHT EMITTING MATERIAL, PREPARATION METHOD THEREOF, AND ORGANIC LIGHT EMITTING DEVICE

(71) Applicant: WUHAN CHINA STAR OPTOELECTRONICS SEMICONDUCTOR DISPLAY TECHNOLOGY CO., LTD., Hubei (CN)

(72) Inventor: Yamin Wang, Hubei (CN)

(73) Assignee: WUHAN CHINA STAR OPTOELECTRONICS SEMICONDUCTOR DISPLAY TECHNOLOGY CO., LTD., Hebei (CN)

( * ) Notice: Subject to any disclaimer, the term of this patent is extended or adjusted under 35 U.S.C. 154(b) by 440 days.

(21) Appl. No.: 16/607,282

(22) PCT Filed: Jun. 11, 2019

(86) PCT No.: PCT/CN2019/090621
§ 371 (c)(1),
(2) Date: Oct. 22, 2019

(87) PCT Pub. No.: WO2020/232770
PCT Pub. Date: Nov. 26, 2020

(65) Prior Publication Data
US 2021/0359218 A1    Nov. 18, 2021

(30) Foreign Application Priority Data

May 21, 2019    (CN) .......................... 201910424571.0

(51) Int. Cl.
*H01L 51/00*    (2006.01)
*B01J 31/24*    (2006.01)
(Continued)

(52) U.S. Cl.
CPC .......... *H01L 51/0071* (2013.01); *B01J 31/24* (2013.01); *C07D 413/14* (2013.01); *C09K 11/06* (2013.01);
(Continued)

(58) Field of Classification Search
CPC ............. H01L 51/0071; H01L 51/0003; H01L 51/5012; H01L 51/56; H01L 51/007; C07D 413/14; C09K 11/06
See application file for complete search history.

(56) References Cited

U.S. PATENT DOCUMENTS 6,057,048 A    5/2000  Hu et al.
7,871,713 B2*  1/2011  Kita ..................... H01L 51/006
                                              252/301.16
(Continued)

FOREIGN PATENT DOCUMENTS

CN    1546477 A    11/2004
CN    101265258 A   9/2008
(Continued)

*Primary Examiner* — Nicholas J Tobergte

(57) ABSTRACT

An organic light emitting material, a preparation method thereof, and an organic light emitting device are provided. The organic light emitting material includes oxadiazole-p-benzodioxazoles. The oxadiazole-p-benzodioxazoles has a large π-conjugated system, that is, it has good planarity and strong visible π-π* absorption. Also, it has high fluorescence quantum yield. Therefore, the oxadiazole-p-benzodioxazoles with a large π-conjugated system has a high-efficiency electron transport property, and it has a high-efficiency electron-withdrawing group to increase electron transport efficiency and improves its luminous efficiency.

10 Claims, 2 Drawing Sheets

(51) Int. Cl.
*C07D 413/14* (2006.01)
*C09K 11/06* (2006.01)
*H01L 51/50* (2006.01)
*H01L 51/56* (2006.01)

(52) U.S. Cl.
CPC ............ *C09K 2211/1007* (2013.01); *C09K 2211/1018* (2013.01); *H01L 51/0003* (2013.01); *H01L 51/5012* (2013.01); *H01L 51/56* (2013.01)

(56) References Cited

U.S. PATENT DOCUMENTS

| | | | | |
|---|---|---|---|---|
| 8,449,989 | B2* | 5/2013 | Kim | C07D 487/22 |
| | | | | 313/506 |
| 9,365,585 | B2* | 6/2016 | Mitchell | C09K 19/3491 |
| 9,882,145 | B2* | 1/2018 | Lee | H01L 51/0052 |
| 9,954,181 | B2* | 4/2018 | Heo | C07D 409/14 |
| 10,833,278 | B2* | 11/2020 | Han | C07D 403/10 |
| 2008/0233429 | A1* | 9/2008 | Oguma | C08G 61/00 |
| | | | | 528/391 |
| 2014/0191160 | A1* | 7/2014 | Ishii | H01L 51/5012 |
| | | | | 524/185 |
| 2015/0243891 | A1 | 8/2015 | Kato et al. | |
| 2017/0098780 | A1 | 4/2017 | Kim et al. | |
| 2018/0123043 | A1 | 5/2018 | Kato et al. | |
| 2019/0097143 | A1 | 3/2019 | Kim et al. | |
| 2020/0207748 | A1* | 7/2020 | Suruga | H01L 51/4273 |
| 2020/0373500 | A1* | 11/2020 | Kase | H01L 51/0071 |

FOREIGN PATENT DOCUMENTS

| | | |
|---|---|---|
| CN | 101812057 A | 8/2010 |
| CN | 104583176 A | 4/2015 |
| CN | 106831650 A | 6/2017 |
| CN | 107254033 A | 10/2017 |
| CN | 108101941 A | 6/2018 |
| CN | 108276558 A | 7/2018 |
| KR | 20170040697 A | 4/2017 |

* cited by examiner

ORGANIC LIGHT EMITTING MATERIAL, PREPARATION METHOD THEREOF, AND ORGANIC LIGHT EMITTING DEVICE

BACKGROUND OF INVENTION

Field of Invention

The present invention relates to a field of display technology, and more particularly, to an organic light emitting material, a preparation method thereof, and an organic light emitting device.

Description of Prior Art

Currently, organic light emitting materials have achieved world renowned results, and flexible organic light emitting diode (OLED) display screens are developed by many companies, and various flexible screens have been achieved. However, there are many problems in the light emitting materials of the flexible OLED display screens, for example, cost, stability of the organic light emitting device, or the durability of the light emitting materials. Therefore, developing host material of light emitting layer in the organic light emitting device is very important. Furthermore, it is very important to develop the host material of the light emitting layer to have a long lifetime, high efficiency, and stable performance, and now it is still an important goal.

SUMMARY OF INVENTION

An organic light emitting material, a preparation method thereof, and an organic light emitting device are provided. The organic light emitting material includes oxadiazole-p-benzodioxazoles, which has a large π-conjugated system to improve luminous efficiency of the organic light emitting material.

In one embodiment, an organic light emitting material includes oxadiazole-p-benzodioxazoles having a structural formula as follows:

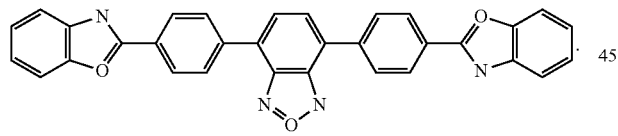

In another embodiment, a preparation method for the oxadiazole-p-benzodioxazoles includes steps as follows:

providing 1,3-benzoxazole-2-phenylboronic acid and 4,7-dibromo-2,1,3-benzoxadiazole;

adding boric acid, 4,7-dibromo-2,1,3-benzoxadiazole, potassium carbonate, and dimethylformamide solvent to a first round bottom flask and stirring continued for 1-3 hours under nitrogen atmosphere;

heating the first round bottom flask to a temperature from 40° C. to 70° C.;

adding the 1,3-benzoxazole-2-phenylboronic acid and a first catalyst to the first round bottom flask and heating continually the first round bottom flask to a temperature from 80° C. to 100° C., and then reacting for 24-94 hours;

cooling the first round bottom flask to room temperature to obtain a first mixture solution; and extracting and drying the first mixture solution to obtain the oxadiazole-p-benzodioxazoles.

In one embodiment, a mole ratio of 1,3-benzoxazole-2-phenylboronic acid to 4,7-dibromo-2,1,3-benzoxadiazole is 1:1.5 to 1:2.

In one embodiment, the first catalyst is tetrakis(triphenylphosphine)palladium.

In one embodiment, the providing 1,3-benzoxazole-2-phenylboronic acid comprises steps as follows:

preparing p-bromobenzoxazole;

adding the p-bromobenzoxazole and tetrahydrofuran solution to a second round bottom flask under argon atmosphere, stirring and dissolving;

cooling through water, wherein a temperature is lowered to −70° C. to 90° C., a second catalyst is added dropwise for 1-3 hours.

performing a reaction for 2-5 hours after dropwise adding the second catalyst;

adding trimethyl borate to the second round bottom flask reacting for 2-5 hours to obtain a second mixture solution; and adding dilute hydrochloric acid to second mixture solution, stirring until to obtain white solid precipitates, filtrating, and drying to obtain the 1,3-benzoxazole-2-phenylboronic acid.

In one embodiment, the second catalyst is butyl lithium.

In one embodiment, preparing the p-bromobenzoxazole includes steps as follows:

providing an o-aminophenol solution and a p-bromobenzoic acid solution;

adding the o-aminophenol solution dissolved in dichloromethane and continuously stirring under nitrogen atmosphere;

adding the p-bromobenzoic acid solution dissolved in the dichloromethane at room temperature for 3-12 hours to obtain a reaction solution; and adding anhydrous sodium sulfate to the reaction solution and stirring, extracting with dichloromethane, obtaining white solid precipitates with ethanol, and drying the white solid precipitates to obtain the p-bromobenzoxazole.

In one embodiment, an organic light emitting device includes the oxadiazole-p-benzodioxazoles.

In one embodiment, an organic light emitting diode device includes:

a first electrode;

a hole injection layer disposed on the first electrode;

a hole transport layer disposed on the hole injection layer;

a light emitting layer disposed on the hole transport layer, wherein the light emitting layer includes the oxadiazole-p-benzodioxazoles;

an electron transport layer disposed on the light emitting layer;

an electron injection layer disposed on the electron transport layer; and a second electrode disposed on the electron injection layer.

In one embodiment, the first electrode is an anode and the second electrode is a cathode.

An organic light emitting material, a preparation method thereof, and an organic light emitting device are provided. The organic light emitting material includes oxadiazole-p-benzodioxazoles. The oxadiazole-p-benzodioxazoles has a large π-conjugated system, that is, it has good planarity and strong visible π-π* absorption. Also, it has high fluorescence quantum yield. Therefore, the oxadiazole-p-benzodioxazoles with a large π-conjugated system has a high-efficiency electron transport property, and it has a high-efficiency electron-withdrawing group to increase electron transport efficiency and improves its luminous efficiency.

BRIEF DESCRIPTION OF DRAWINGS

In order to more clearly illustrate the technical solutions in the embodiments of the present invention, the drawings used in the description of the embodiments will be briefly described below. It is obvious that the drawings in the following description are only some embodiments of the present invention. Other drawings can also be obtained from those skilled persons in the art based on these drawings without paying any creative effort.

It is further to explain the present invention below with the drawings and embodiments.

Figure 1:
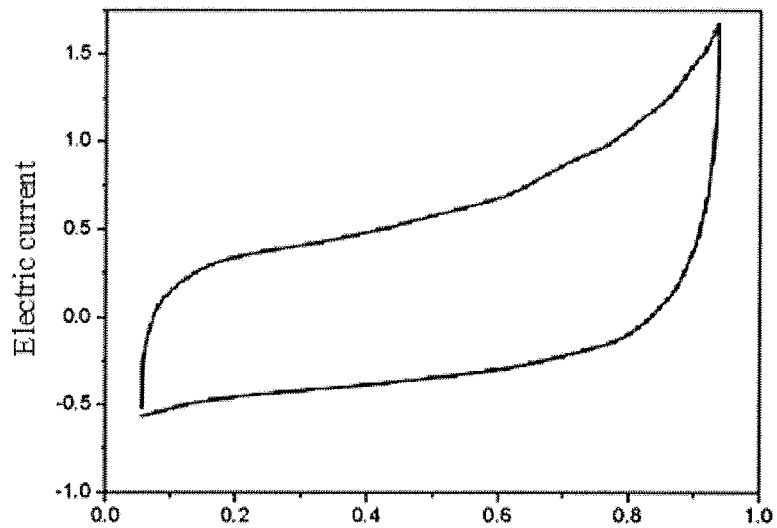
FIG. 1 is a waveform diagram of the oxadiazole-p-benzodioxazoles according one embodiment of the present invention as determined by cyclic voltammetry.

REFERENCE MARK organic light emitting device: 1;
first electrode: 11;
hole injection layer: 12;
hole transport layer: 13;
light emitting layer: 14;
electron transport layer: 15;
electron injection layer: 16; and
second electrode: 17.

DETAILED DESCRIPTION OF PREFERRED EMBODIMENTS

The embodiments of the present invention are described in detail below, and the embodiments are illustrated in the drawings. The same or similar reference numerals indicate the same or similar elements or elements having the same or similar functions. The embodiments described below with reference to the drawings are intended to be illustrative of the invention and are not to be limited.

The following description of the embodiments is provided by reference to the following drawings. Directional terms mentioned in this application, such as "up," "down," "forward," "backward," "left," "right," "inside," "outside," "side," etc., are merely indicated the direction of the drawings. Therefore, the directional terms are used for illustrating and understanding of the application rather than limiting thereof. In the figures, elements with similar structure are indicated by the same reference numerals.

An organic light emitting material includes oxadiazole-p-benzodioxazoles having a structural formula as follows:

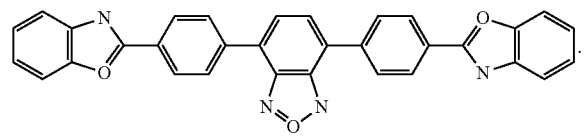

The oxadiazole-p-benzodioxazoles has a large π-conjugated system, that is, it has good planarity and strong visible π-π* absorption. Also, it has high fluorescence quantum yield. Therefore, the oxadiazole-p-benzodioxazoles with a large π-conjugated system has a high-efficiency electron transport property, and it has a high-efficiency electron-withdrawing group to increase electron transport efficiency and improves its luminous efficiency.

Furthermore, a preparation method for the oxadiazole-p-benzodioxazoles, includes steps as follows:

providing 1,3-benzoxazole-2-phenylboronic acid and 4,7-dibromo-2,1,3-benzoxadiazole;

Before the step of providing the 1,3-benzoxazole-2-phenylboronic, it is necessary to prepare a raw material, which is p-bromobenzoxazole, for the synthesis of 1,3-benzoxazole-2-phenylboronic. In the embodiment, the preparation process of p-bromobenzoxazole is described as follows:

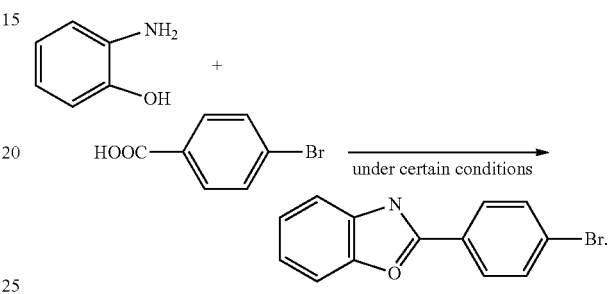

Specifically, the preparation method for the p-bromobenzoxazole includes steps as follows:

providing an o-aminophenol solution and a p-bromobenzoic acid solution; adding the o-aminophenol solution dissolved in dichloromethane and continuously stirring under nitrogen atmosphere; adding the p-bromobenzoic acid solution dissolved in the dichloromethane at room temperature for 3-12 hours to obtain a reaction solution; and adding anhydrous sodium sulfate to the reaction solution and stirring, extracting with dichloromethane, obtaining white solid precipitates with ethanol, and drying the white solid precipitates to obtain the p-bromobenzoxazole.

After preparing the p-bromobenzoxazole, it starts to prepare 1,3-benzoxazole-2-phenylboronic acid. In the embodiment, the preparation process of 1,3-benzoxazole-2-phenylboronic acid is described as follows:

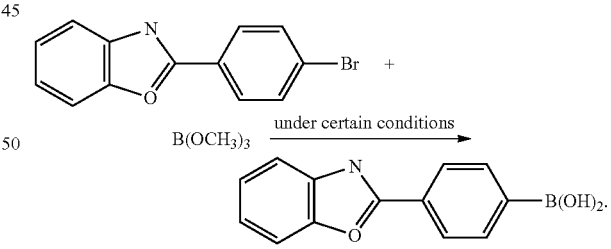

Specifically, the preparation method for 1,3-benzoxazole-2-phenylboronic acid includes steps as follows:

adding the p-bromobenzoxazole and tetrahydrofuran solution to a second round bottom flask under argon atmosphere, stirring and dissolving; cooling through water, and a temperature is lowered to −70° C. to 90° C., a second catalyst, which is butyl lithium, is added dropwise for 1-3 hours; performing a reaction for 2-5 hours after dropwise adding the second catalyst; adding trimethyl borate to the second round bottom flask reacting for 2-5 hours to obtain a second mixture solution; and adding dilute hydrochloric acid to second mixture solution, stirring until to obtain white solid precipitates, filtrating, and drying to obtain the 1,3-benzoxazole-2-phenylboronic acid.

Finally, oxadiazole-p-benzodioxazoles is prepared after preparing the p-bromobenzoxazole. The preparation process of oxadiazole-p-benzodioxazoles is described as follows:

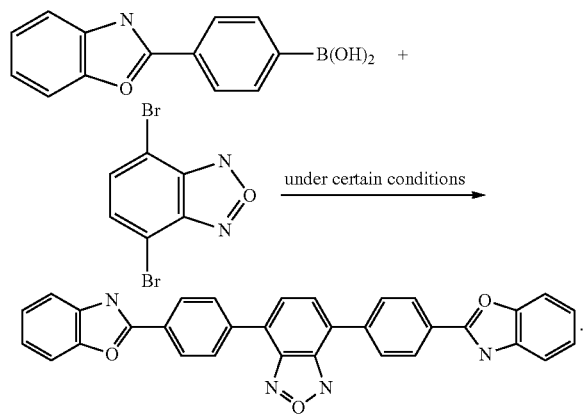

Specifically, a preparation method for the oxadiazole-p-benzodioxazoles includes steps as follows:
adding boric acid, 4,7-dibromo-2,1,3-benzoxadiazole, potassium carbonate, and dimethylformamide solvent to a first round bottom flask and stirring continued for 1-3 hours under nitrogen atmosphere; heating the first round bottom flask to a temperature from 40° C. to 70° C.; adding the 1,3-benzoxazole-2-phenylboronic acid and a first catalyst, which is tetrakis(triphenylphosphine)palladium, to the first round bottom flask and heating continually the first round bottom flask to a temperature from 80° C. to 100° C., and then reacting for 24-94 hours; cooling the first round bottom flask to room temperature to obtain a first mixture solution; and extracting and drying the first mixture solution to obtain the oxadiazole-p-benzodioxazoles. A mole ratio of 1,3-benzoxazole-2-phenylboronic acid to 4,7-dibromo-2,1,3-benzoxadiazole is 1:1.5 to 1:2.

Then, the oxadiazole-p-benzodioxazoles is analyzed. Firstly, the functional analysis and energy level calculation are carried out according to the structural formula of the oxadiazole-p-benzodioxazoles. The highest occupied molecular orbital (HOMO) level is 4.78 eV and the lowest unoccupied molecular orbit (LUMO) level is 2.03 eV, and an energy level difference is 2.43 eV. The HOMO level oxadiazole-p-benzodioxazoles, which is 4.78 eV is less than HOMO level of indium tin oxide. A conductive substrate made of the indium tin oxide conductive substrate has a work function of 5.3. Therefore, the oxadiazole-p-benzodioxazoles is theoretically conformed to the work function of the host material of the light emitting layer in the organic light emitting device. The energy level difference of oxadiazole-p-benzodioxazoles is effective to improve the luminous efficiency and luminescence ability of the device.

Figure 2:
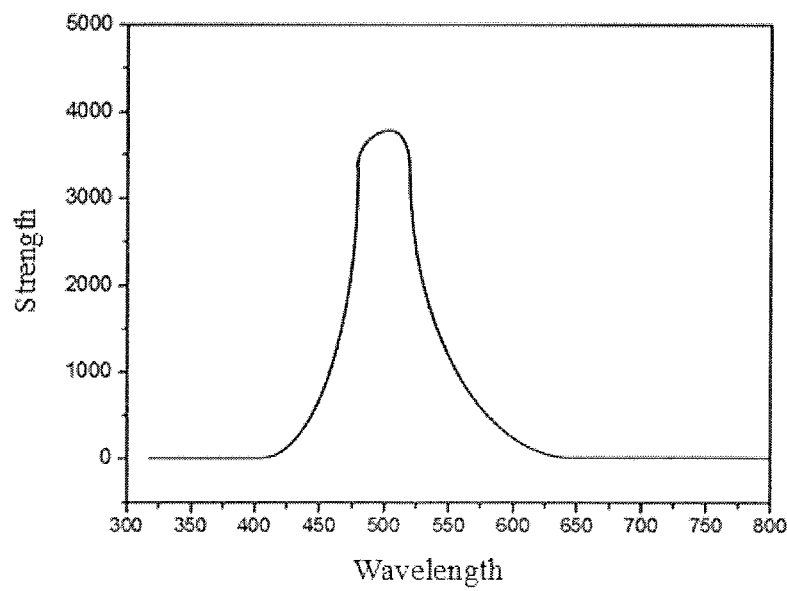
FIG. 2 is a fluorescence spectrum showing the oxadiazole-p-benzodioxazoles in the tetrahydrofuran solution.

Next, the ferrocene/ferrocene ion is used as the internal standard, the initial oxidation-reduction potential E1/2 of the oxadiazole-p-benzodioxazoles in the ammonium hexafluorophosphate medium is determined by cyclic voltammetry. Specifically, the oxadiazole-p-benzodioxazoles is prepared as a 0.1 mol/L electrolyte solution, and then a $1\times10^{-6}$ mol/L solution including tetrahydrofuran and oxadiazole-p-benzodioxazoles is prepared. Then, a waveform diagram determined by the cyclic voltammetry is obtained by performing an electrode scanning cycle with a scan rate 100 mV/s for 10 times under an argon atmosphere. As shown in FIG. 1, it can be seen that EHOMO=e(E1/2|+4.4), ELUMO=EHOMO−|Eg|, and Eg=1240/λ. As shown in FIG. 2, the wavelength λ is 510 nm. The HOMO and LUMO values of the oxadiazole-p-benzodioxazoles are 4.78 e V and 2.03 e V, respectively, and the energy level difference can effectively balance the electron transport, and thus oxadiazole-p-benzodioxazoles can be used as the light emitting layer in the organic light emitting device.

Figure 3:
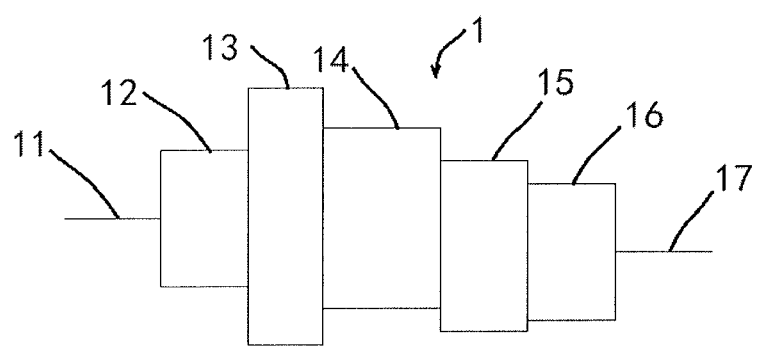
FIG. 3 is a structural view of an organic light emitting device according to one embodiment of the present invention.

As shown in FIG. 3, an organic light emitting device 1 includes the oxadiazole-p-benzodioxazoles. In the embodiment, the organic light emitting device includes a first electrode 11, a hole injection layer 12, a hole transport layer 13, a light emitting layer 14, an electron transport layer 15, an electron injection layer 16, and a second electrode 17. The hole injection layer 12 is disposed on the first electrode 11. The hole transport layer 13 is disposed on the hole injection layer 12. The light emitting layer 14 is disposed on the hole transport layer 13. The light emitting layer 14 has the oxadiazole-p-benzodioxazoles. The electron transport layer 15 is disposed on the light emitting layer 14. The electron injection layer 16 is disposed on the electron transport layer 15. The second electrode 17 is disposed on the electron injection layer 16. The first electrode 11 is an anode and the second electrode 17 is a cathode.

In the above, the present application has been described in the above preferred embodiments, but the preferred embodiments are not intended to limit the scope of the invention, and a person skilled in the art may make various modifications without departing from the spirit and scope of the application. The scope of the present application is determined by claims.

What is claimed is:
1. An organic light emitting material, comprising oxadiazole-p-benzodioxazoles having a structural formula as follows:

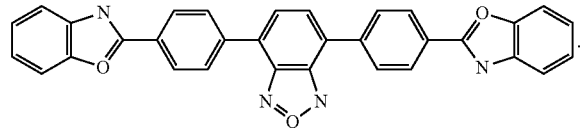

2. A preparation method for the oxadiazole-p-benzodioxazoles of claim 1, comprising steps as follows:
providing 1,3-benzoxazole-2-phenylboronic acid and 4,7-dibromo-2,1,3-benzoxadiazole;
adding boric acid, 4,7-dibromo-2,1,3-benzoxadiazole, potassium carbonate, and dimethylformamide solvent to a first round bottom flask and stirring continued for 1-3 hours under nitrogen atmosphere;
heating the first round bottom flask to a temperature from 40° C. to 70° C.;
adding the 1,3-benzoxazole-2-phenylboronic acid and a first catalyst to the first round bottom flask and heating continually the first round bottom flask to a temperature from 80° C. to 100° C., and then reacting for 24-94 hours;
cooling the first round bottom flask to room temperature to obtain a first mixture solution; and
extracting and drying the first mixture solution to obtain the oxadiazole-p-benzodioxazoles.

3. The preparation method according to claim 2, wherein a mole ratio of 1,3-benzoxazole-2-phenylboronic acid to 4,7-dibromo-2,1,3-benzoxadiazole is 1:1.5 to 1:2.

4. The preparation method according to claim 3, wherein the first catalyst is tetrakis(triphenylphosphine)palladium.

5. The preparation method according to claim 2, wherein the providing 1,3-benzoxazole-2-phenylboronic acid comprises steps as follows:
  preparing p-bromobenzoxazole;
  adding the p-bromobenzoxazole and tetrahydrofuran solution to a second round bottom flask under argon atmosphere, stirring and dissolving;
  cooling through water, wherein a temperature is lowered to −70° C. to 90° C., a second catalyst is added dropwise for 1-3 hours.
  performing a reaction for 2-5 hours after dropwise adding the second catalyst;
  adding trimethyl borate to the second round bottom flask reacting for 2-5 hours to obtain a second mixture solution; and
  adding dilute hydrochloric acid to second mixture solution, stirring until to obtain white solid precipitates, filtrating, and drying to obtain the 1,3-benzoxazole-2-phenylboronic acid.

6. The preparation method according to claim 5, wherein the second catalyst is butyl lithium.

7. The preparation method according to claim 2, wherein preparing the p-bromobenzoxazole comprises steps as follows:
  providing an o-aminophenol solution and a p-bromobenzoic acid solution;
  adding the o-aminophenol solution dissolved in dichloromethane and continuously stirring under nitrogen atmosphere;
  adding the p-bromobenzoic acid solution dissolved in the dichloromethane at room temperature for 3-12 hours to obtain a reaction solution; and
  adding anhydrous sodium sulfate to the reaction solution and stirring, extracting with dichloromethane, obtaining white solid precipitates with ethanol, and drying the white solid precipitates to obtain the p-bromobenzoxazole.

8. An organic light emitting device, comprising the oxadiazole-p-benzodioxazoles of claim 1.

9. The organic light emitting diode device according to claim 8, comprising:
  a first electrode;
  a hole injection layer disposed on the first electrode;
  a hole transport layer disposed on the hole injection layer;
  a light emitting layer disposed on the hole transport layer, wherein the light emitting layer comprises the oxadiazole-p-benzodioxazoles;
  an electron transport layer disposed on the light emitting layer;
  an electron injection layer disposed on the electron transport layer; and
  a second electrode disposed on the electron injection layer.

10. The organic light emitting diode device according to claim 9, wherein the first electrode is an anode and the second electrode is a cathode.

* * * * *